US009016563B2

(12) United States Patent
Zerhusen et al.

(10) Patent No.: US 9,016,563 B2
(45) Date of Patent: *Apr. 28, 2015

(54) OPTICAL DETECTOR AT POINT OF CARE

(71) Applicant: Hill-Rom Services, Inc., Batesville, IN (US)

(72) Inventors: Robert M. Zerhusen, Cincinnati, OH (US); Stephen C. Flint, Fortville, IN (US); Dan R. Tallent, Hope, IN (US); Jack B. Sing, Batesville, IN (US); Keith A. Huster, Sunman, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/141,917

(22) Filed: Dec. 27, 2013

(65) Prior Publication Data
US 2014/0191038 A1 Jul. 10, 2014

Related U.S. Application Data

(63) Continuation of application No. 13/075,243, filed on Mar. 30, 2011, now Pat. No. 8,616,438.

(51) Int. Cl.
G06F 17/00 (2006.01)
G06F 19/00 (2011.01)

(52) U.S. Cl.
CPC .............. *G06F 19/36* (2013.01); *G06F 19/327* (2013.01); *G06F 19/3418* (2013.01)

(58) Field of Classification Search
USPC ............... 235/375, 492, 487, 462.13, 462.14, 235/462.46, 472.02
See application file for complete search history.

(56) References Cited

U.S. PATENT DOCUMENTS

| 4,811,435 | A | 3/1989 | Foster et al. |
| 4,850,009 | A | 7/1989 | Zook et al. |
| 4,857,716 | A | 8/1989 | Gombrich et al. |
| 5,640,953 | A | 6/1997 | Bishop et al. |
| 5,771,511 | A | 6/1998 | Kummer et al. |
| 5,781,442 | A * | 7/1998 | Engleson et al. ............. 700/214 |
| 5,914,701 | A | 6/1999 | Gersheneld et al. |
| 6,171,264 | B1 | 1/2001 | Bader |
| 6,190,326 | B1 | 2/2001 | McKinnon et al. |
| 6,287,252 | B1 | 9/2001 | Lugo |
| 6,478,748 | B1 | 11/2002 | Kuhn et al. |
| 6,487,735 | B1 * | 12/2002 | Jacques et al. ..................... 5/424 |
| 6,671,563 | B1 | 12/2003 | Engelson et al. |
| 7,480,951 | B2 | 1/2009 | Weismiller et al. |
| 7,784,125 | B2 * | 8/2010 | Morin et al. ....................... 5/430 |

(Continued)

*Primary Examiner* — Daniel St Cyr
(74) *Attorney, Agent, or Firm* — Barnes & Thornburg LLP

(57) ABSTRACT

A patient support apparatus including a barrier, an optical detector, and a control system. The optical detector secured to the barrier and configured to detect indicia having a predetermined pattern. The control system includes a processor in communication with the optical detector, a transmitter in communication with the processor, and a memory unit in communication with the processor. The memory unit stores a unique identifier associated with the patient support apparatus. The processor receiving a signal from the optical detector indicative of data detected by the optical detector and performing a set of instructions in response to the optical detector communicating the data, the set of instructions performed by the processor including (i) linking the data with the unique identifier, and (ii) communicating the linked data and unique identifier to a network.

20 Claims, 3 Drawing Sheets

(56) References Cited

U.S. PATENT DOCUMENTS

| | | |
|---|---|---|
| 7,788,369 B2 * | 8/2010 | McAllen et al. ............ 709/224 |
| 7,853,457 B2 | 12/2010 | Klabunde et al. |
| 7,868,740 B2 | 1/2011 | McNeely et al. |
| 8,616,438 B2 * | 12/2013 | Zerhusen et al. ............ 235/375 |
| 2002/0013518 A1 | 1/2002 | West et al. |
| 2002/0044059 A1 | 4/2002 | Reeder et al. |
| 2004/0059599 A1 | 3/2004 | McIvor |
| 2004/0100361 A1 | 5/2004 | Brackett et al. |
| 2004/0186358 A1 | 9/2004 | Chernow et al. |
| 2005/0043964 A1 | 2/2005 | Thielscher et al. |
| 2005/0101844 A1 | 5/2005 | Duckert et al. |
| 2005/0131733 A1 | 6/2005 | Lubow |
| 2006/0015589 A1 | 1/2006 | Ang et al. |
| 2010/0306921 A1 | 12/2010 | Kramer |
| 2011/0166891 A1 | 7/2011 | Zerhusen et al. |

* cited by examiner

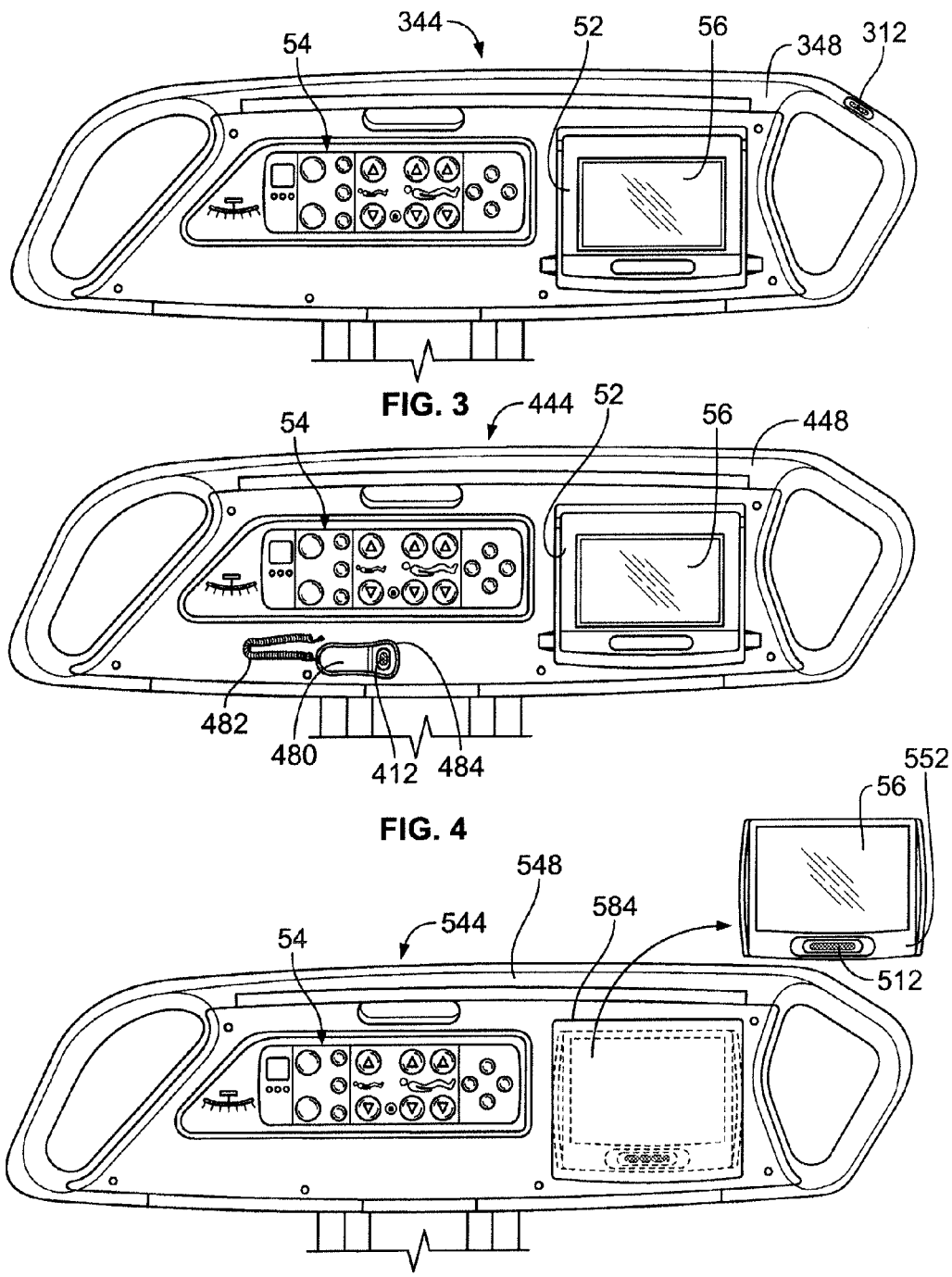

OPTICAL DETECTOR AT POINT OF CARE

RELATED APPLICATIONS

This application is a continuation of U.S. patent application Ser. No. 13/075,243, filed Mar. 30, 2011, now U.S. Pat. No. 8,616,438, which is incorporated herein by this reference.

BACKGROUND

The present disclosure is related to the arrangement and operation of patient support apparatus with a sensor. More specifically, the present disclosure is related a patient support apparatus including an optical detector.

Patient support apparatuses known in the art include barriers, such as siderails and end panels for example, that are coupled to the patient support apparatus and may be positioned to block a patient from entering or exiting a patient support apparatus. Some barriers are equipped with user interfaces having user input devices such as buttons or keyboards for inputting information. Such user input devices sometimes require multiple button presses or keystrokes to enter information into a control system for the patient support.

Entering information with multiple button presses or keystrokes can increase the amount of time a caregiver spends at a patient support apparatus. Additionally, information entered via multiple button presses or keystrokes can include mistakes from time to time.

SUMMARY

The present application discloses one or more of the features recited in the appended claims and/or the following features which, alone or in any combination, may comprise patentable subject matter:

According to the present disclosure, a patient support apparatus may include a barrier, an optical detector, and a control system. The optical detector may be secured to the barrier and may be configured to detect indicia having a predetermined pattern. The control system may include a processor in communication with the optical detector, a transmitter in communication with the processor, and a memory unit in communication with the processor. The memory unit may store a unique identifier associated with the patient support apparatus. The processor may receive a signal from the optical detector indicative of data detected by the optical detector. The processor may also perform a set of instructions in response to the optical detector communicating the data. The set of instructions performed by the processor may include linking the data with the unique identifier and communicating the linked data and unique identifier to a network.

In some embodiments, the barrier may include a siderail and the optical detector may be secured to the siderail. The optical detector may be at least partially disposed in the siderail.

The siderail may include a body and a panel pivotably coupled to the body and the optical detector may be coupled to the panel for pivotable movement relative to the body of the siderail therewith. The panel may include a user interface with a display. The optical detector may be a bar code reader and the indicia may be a bar code. In some embodiments the indicia may be at least two bar codes.

It is contemplated that the data may be associated with a caregiver or a patient. The control system may further include a clock providing a date. The clock may be in communication with the processor. In some embodiments, the set of instructions performed by the processor may also include receiving the date from the clock and communicating the date to the network along with the linked data and unique identifier. The data may be associated with a biologic sample.

The network may include a hospital information system. The network may further include a nurse call system.

In some embodiments, the control system may further include a user interface in communication with the processor. The user interface may have a display and at least one user input device. The set of instructions performed by the processor may further include communicating a prompt to the display, receiving a response to the prompt from the user input device, and communicating the response to the network along with the linked data and unique identifier.

The control system may further include a receiver in communication with the network and the processor and a user interface in communication with the processor. The user interface may have a display. The set of instructions performed by the processor may further include receiving network information from the receiver and communicating the network information to the display of the user interface so that the display is reconfigured to show the network information. In some embodiments, the network information is patient information.

According to another aspect of the present disclosure, a method of monitoring events at a patient support apparatus may include the steps of detecting an indicia of a predetermined pattern with an optical detector coupled to a barrier, linking data communicated from the optical detector with a unique identifier and a date, and communicating the linked data, unique identifier, and date to a network.

In some embodiments, the method may include the steps of displaying a prompt on a display and communicating a response to the prompt to the network along with the linked data, unique patient support identifier, and date. The response to the prompt may be a patient information.

It is contemplated that the method may include the steps of receiving network information associated with the data from the network and displaying the network information on a display coupled to a patient support. The network information may be patient information, caregiver information, technician information, or housekeeper information.

Additional features, which alone or in combination with any other feature(s), including those listed above and those listed in the claims may comprise patentable subject matter and will become apparent to those skilled in the art upon consideration of the following detailed description of illustrative embodiments exemplifying the best mode of carrying out the embodiments as presently perceived.

BRIEF DESCRIPTION OF THE DRAWINGS

The detailed description particularly refers to the accompanying figures in which:

FIG. 3 is a side elevation view of another siderail embodiment and an another optical detector situated inside the alternative siderail;

FIG. 4 is a side elevation view of an another siderail embodiment and an another optical detector that is tethered to the alternative siderail being received in a receiving channel sized to hold the optical detector; and FIG. 5 is a side elevation view of yet another siderail embodiment and an yet another optical detector situated in a panel that is removably received in a receiving channel sized to hold the panel.

DETAILED DESCRIPTION OF THE DRAWINGS

Figure 1:
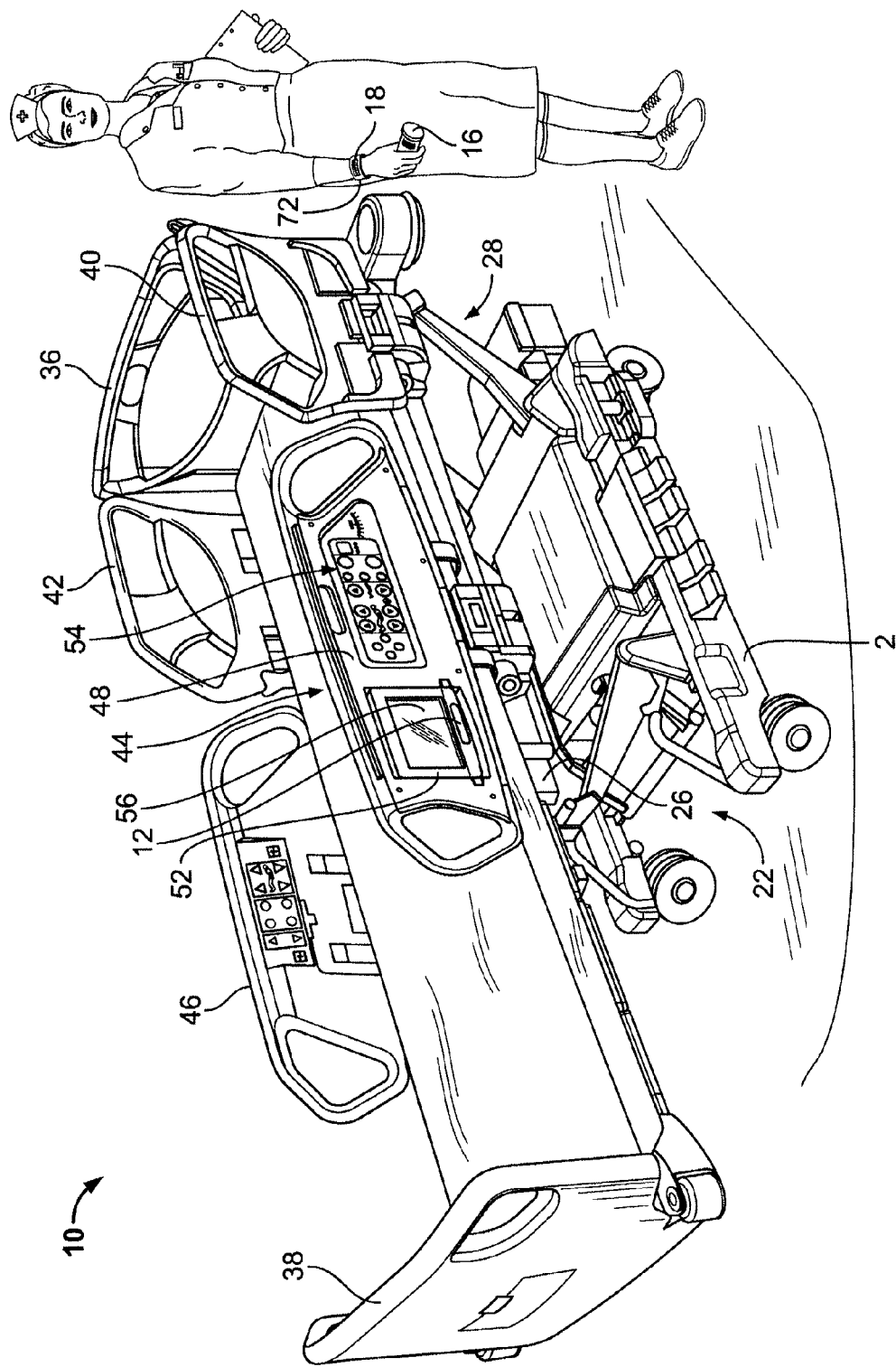
FIG. 1 is a perspective view of the patient support apparatus of the present disclosure including a siderail with an optical detector situated in a panel pivotably coupled to the siderail.

A patient support apparatus shown in FIG. 1 is illustratively embodied as a hospital bed 10. The bed 10 includes an optical detector 12 and a control system 14 (shown diagrammatically in FIG. 2) in communication with the optical detector 12. The optical detector 12 detects indicia 16, 18 with a predetermined pattern and communicates a signal indicative of data from the indicia 16, 18 to the control system 14. In the illustrative embodiment, the data is related to at least one of a caregiver, a patient, a technician, a housekeeper, a blood sample, a urine sample, or another biologic sample. In other embodiments, the data may be related to other personnel or objects. The control system 14 links the data with a unique identifier 15 associated with the bed 10 and communicates the linked data and unique identifier 15 to a hospital information system 20. In the illustrative embodiment, the optical detector 12 is a barcode scanner and the indicia 16, 18 are linear codes similar to UPC codes. In other embodiments, the optical detector 12 may be another optical sensor such as a color sensor, a light intensity sensor, or another suitable sensor. It is contemplated that in other embodiments, the indicia 16, 18 may be other linear codes, bulls eye codes, concentric circle codes, starburst pattern codes, color patterns, lights, or other optically detectable indicia.

The bed 10 includes a frame structure 22 having a lower frame 24 and an upper frame 26 which is movable relative the lower frame 24 via lift arms 28 as shown, for example, in FIG. 1. Lift arms 28 pivot relative to lower frame 24 to raise and lower upper frame 26. The bed 10 also includes an articulating deck 32 driven by a number of deck drivers (not shown) and a mattress 34 supported on the deck 32. The lift arms 28 and the deck drivers, along with other drivers, make up patient support drives 35 (represented diagrammatically in FIG. 2). The bed 10 further includes a headboard 36, a footboard 38, headrails 40 and 42, and siderails 44 and 46.

The siderail 44 includes a body portion 48 and a user interface 50 as shown in FIG. 1. The user interface 50 includes a panel 52 and a series of user input buttons 54. The panel 52 is pivotably coupled to the body portion 48 of the siderail 44 and includes a display 56. The display 56 is illustratively a touch screen LCD and may act as an additional user input device. In the illustrative embodiment, the optical detector 12 is secured to the panel 52 and is pivotable therewith relative to the body portion 48 of the siderail 44. The optical detector 12 is thus always at the bed 10 with a field of view 57 (shown in FIG. 2) near the bed 10 and is powered by the bed 10. In the illustrative embodiment, the optical detector 12 is always scanning for indicia in field of view 57. In other embodiments, optical detector 12 may scan for indicia 16, 18 in field of view 57 in response to motion detected near optical detector 12 by a motion detector included in the bed 10.

Figure 2:
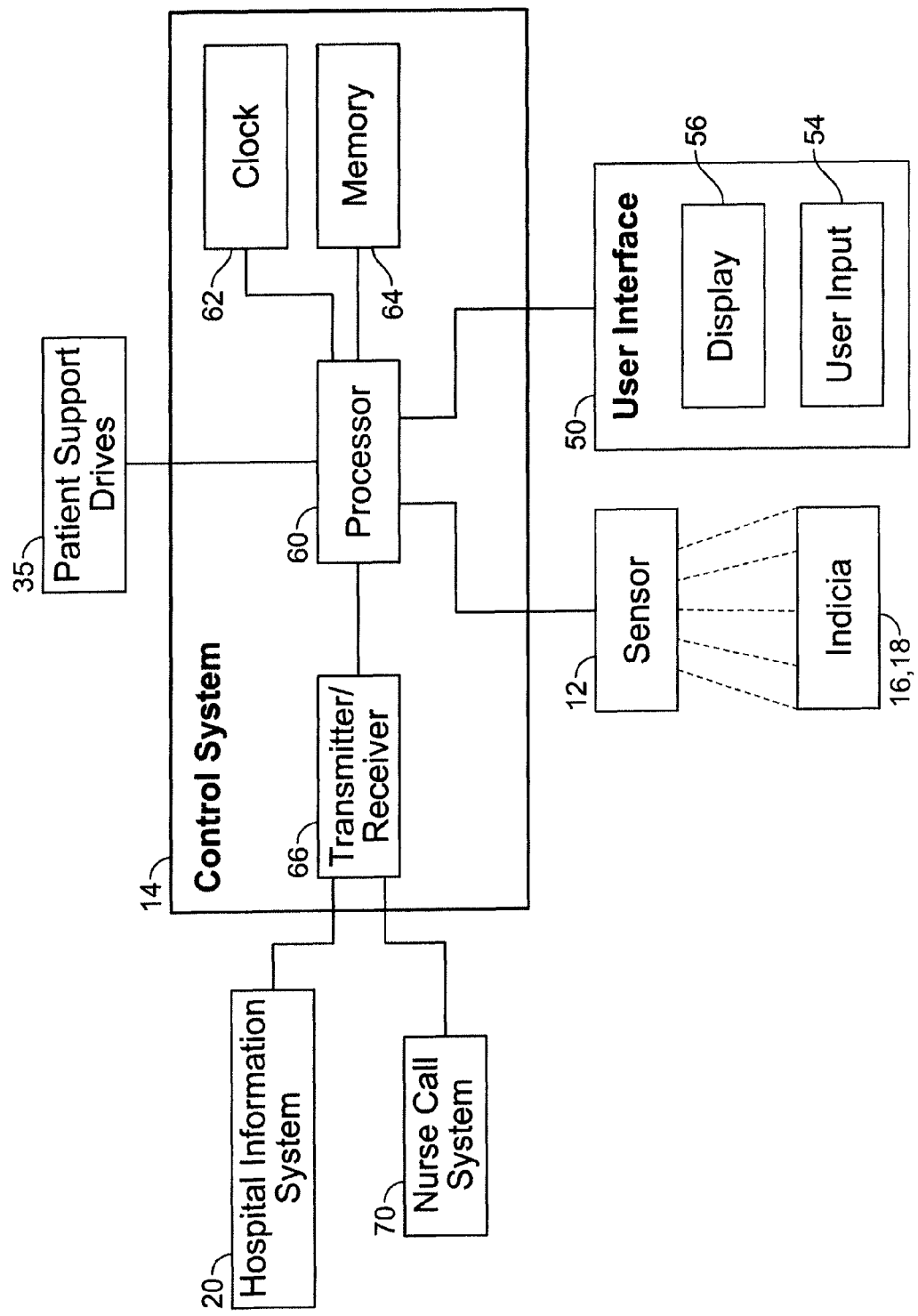
FIG. 2 is a diagrammatic representation of a control system of the patient support apparatus of FIG. 1 along with components in communication with the control system.

Referring to FIG. 2, the control system 14 includes a processor 60, a clock 62, a memory 64 storing the unique identifier 15, and a transceiver 66. The processor 60 is in communication with the clock 62, the memory 64, and the transceiver 66. The clock 62 communicates a current time and date to the processor 60. The memory 64 communicates the unique identifier 15 to the processor 60 and stores instructions for the processor 60 to perform. In some embodiments, the memory 64 may be re-writable memory.

The transceiver 66 is in communication with the hospital information system 20 and a nurse call system 70 as suggested by FIG. 2. The transceiver 66 sends information from the processor 60 to the hospital information system 20 and to the nurse call system 70. The transceiver 66 also receives information from the hospital information system 20 and the nurse call system 70 and communicates that information to the processor 60. In the illustrative embodiment, the transceiver 66 is a wireless RF communication device as is well known in the art. In other embodiments, the transceiver 66 may be another wireless or wired device. It is also contemplated that in other embodiments the transceiver 66 may be made up of separate components, one component for transmitting information and another component for receiving information.

The processor 60 is also in communication with the user interface 50, patient support drives 35, and the optical detector 12 as suggested, for example, in FIG. 2. The processor 60 receives inputs from the user input buttons 54 and the touch screen display 56 of the user interface 50. The processor 60 also sends screens and prompts to the display 56 of the user interface 50 for user interaction. The processor 60 further directs the patient support drives 35 to move the bed 10 into different configurations. In some embodiments, the optical detector 12 may scan for indicia 16, 18 in the field of view 57 in response to a user input received by the processor 60 from the user input buttons 54 or from the display 56.

In the illustrative embodiment, when the optical detector 12 detects the indicia 16, 18, the optical detector 12 communicates a signal indicative of data from the indicia 16, 18 to the processor 60. In response to receiving the data from the optical detector 12, the processor 60 links the data with the unique identifier 15 stored in the memory 64. The processor 60 then communicates the linked data and the unique identifier 15 to the transceiver 66. The transceiver 66 sends the linked information to the hospital information system 20 and the nurse call system 70 for storage, display, and analysis. In some embodiments, the time and date provided by the clock 62 may also be linked with the data provided by the optical detector 12 and the unique identifier 15 provided by the memory 64.

In some embodiments, the hospital information system 20 may send network information such as patient information, caregiver information, or other information back to the transceiver 66 in response to the hospital information system 20 receiving linked information from the transceiver 66. In such embodiments, the processor 60 may receive the network information and communicate it to the display 56 so that the network information is shown on the display 56.

In one example of the illustrative embodiment, a patient bracelet having indicia (not shown) is detected by the optical detector 12. Additionally, the indicia 16 on a biologic sample container 71 is detected by the optical detector 12. Then data from the indicia 16 is communicated by the optical detector 12 to the processor 60. The processor 60 then links the data with the unique identifier 15 from the memory 64. The linked information is then communicated by the processor 60 to the transceiver 66. The transceiver 66 sends the linked information to the hospital information system 20 and the nurse call system 70. Then the hospital information system 20 and nurse call system 70 identifies a patient name and sample number associated with the data from the patient bracelet and the biologic sample container 71, thereby ensuring that a particular patient has given a biologic sample.

In another example of the illustrative embodiment, when a caregiver enters a room with the bed 10, the indicia 18 on a bracelet 72, as shown, for example, in FIG. 1, is detected by the optical detector 12. Then, data from the indicia 18 is communicated by the optical detector to the processor 60. The processor 60 then links the data with a time and date from the clock 62 and the unique identifier 15 from the memory 64. The linked information is then communicated by the processor 60 to the transceiver 66. The transceiver 66 sends the linked information to the hospital information system 20 and the nurse call system 70. Then the hospital information system 20 and the nurse call system 70 identifies a caregiver name associated with the data from indicia 18 on the caregiver bracelet 72 so that a user can monitor the frequency of caregiver visits to a particular bed 10 determined from the linked information.

In some embodiments, when the optical detector 12 communicates data from detected indicia 16, 18 to the processor 60, the processor 60 communicates a prompt to the display 56 of the user interface 50. The prompt may be communicated to the processor 60 from the memory 64 or from the hospital information system 20 via the transceiver 66. A user may input a response via the user interface 50 in response to the prompt that is communicated to the processor 60. Then, the processor 60 may link the response with the data from the optical detector 12, the time and date from the clock 62, and with the unique identifier 15 from the memory 64. The linked information may be communicated by the processor 60 to the transceiver 66 and sent on to the hospital information system 20 and nurse call system 70.

In one example of such an embodiment, when a caregiver enters a room with the bed 10, the indicia 18 on bracelet 72 is detected by the optical detector 12 as suggested in FIG. 1. Then, data from the indicia 18 is communicated by the optical detector to the processor 60. The processor 60 may then communicate a prompt previously provided by the hospital information network 20 via the transceiver 66 to the display 56 showing a patient name linked with the bed 10 and asking what blood pressure the caregiver has determined for the patient linked with the bed 10. The caregiver may respond to the prompt by inputting a response indicating a blood pressure by using the touch screen display 56 of the user interface. The processor 60 then links the blood pressure from the display 56, the data from indicia 16, the time and date from the clock 62, and the unique identifier 15 from the memory 64. The linked information is communicated by the processor 60 to the transceiver 66. The transceiver 66 sends the linked information to the hospital information system 20 and the nurse call system 70. Then the hospital information system 20 and the nurse call system 70 identifies a caregiver name associated with the data from the indicia 18 on the bracelet 72, for example, monitoring caregiver task completion determined from the linked information.

Another optical detector 312 and another siderail 344 are shown in FIG. 3. The optical detector 312 is operationally similar to optical detector 12 and is configured for use with the above described control system 14. The siderail 344 is substantially similar to the siderail 44 described above and similar features are indicated with like reference numbers.

The optical detector 312 is spaced apart from the pivotable panel 52 of the siderail 344 and the optical detector 312 is disposed inside the siderail 344, as shown, for example, in FIG. 3. The siderail 344 has a body portion 348 configured to house the optical detector 312. The optical detector 312 is not movable relative to the body portion 348 of the siderail 344.

Another optical detector 412 and another siderail 444 are shown in FIG. 4. The optical detector 412 is operationally similar to optical detector 12 and is configured for use with the above described control system 14. The siderail 444 is substantially similar to the siderail 44 described above and similar features are indicated with like reference numbers.

The optical detector 412 is housed in a pod 480 that is movable relative to the siderail 444. The caregiver pod 480 is coupled to the siderail 444 by an extendable tether 482 shown in FIG. 4. The tether 482 is configured to keep the alternative optical detector 412 with the siderail 444 as the bed 10 is moved from location to location. In some embodiments, the tether 482 may also serve as a communication line between the optical detector 412 and the control system 14.

The siderail 444 has a body portion 448 that is formed to include a receiving channel 484 sized to receive the pod 480 as shown in FIG. 4. When the pod 480 is received in the receiving channel 484, the optical detector 412 faces out so that the optical detector 412 can detect indicia 16, 18 without being moved relative to the siderail 444.

Yet another alternative optical detector 512 and another alternative siderail 544 are shown in FIG. 5. The optical detector 512 is operationally similar to optical detector 12 and is configured for use with the above described control system 14.

The siderail 544 includes a body portion 548 that is formed to include a receiving channel 584 and a user interface 550 as shown, for example, in FIG. 5. The user interface 550 includes a removable panel 552 in wireless communication with the control system 14 and a series of user input buttons 554. The panel 552 is removably stored in the receiving channel 584 and includes a display 56 as suggested in FIG. 5. The optical detector 512 is coupled to the panel 552 and is movable therewith relative to the siderail 544. The optical detector 512 is also in wireless communication with the control system 14. When the panel 552 is received in the receiving channel 584, the optical detector 512 and display 56 face outwardly so that the optical detector 512 can detect indicia without being moved relative to the siderail 544.

Although certain illustrative embodiments have been described in detail above, variations and modifications exist within the scope and spirit of this disclosure as described and as defined in the following claims.

The invention claimed is:

1. A patient support apparatus comprising
an optical detector and configured to detect indicia having a predetermined pattern, and
a control system including a processor in communication with the optical detector, a transmitter in communication with the processor, and a memory unit in communication with the processor, the memory unit storing a unique identifier associated with the patient support apparatus,
wherein the processor receives a signal from the optical detector indicative of data detected by the optical detector and performs a set of instructions in response to the optical detector communicating the data, the set of instructions performed by the processor including (i) linking the data with the unique identifier, and (ii) communicating the linked data and unique identifier to a network.

2. The patient support apparatus of claim 1, wherein the optical detector is secured to a barrier.

3. The patient support apparatus of claim 2, wherein the barrier includes a siderail and the optical detector is at least partially disposed in the siderail.

4. The patient support apparatus of claim 2, wherein the siderail includes a body and a panel pivotably coupled to the body and the optical detector is at coupled to the panel for pivotable movement relative to the body of the siderail therewith.

5. The patient support apparatus of claim 4, wherein the panel includes a user interface with a display.

6. The patient support apparatus of claim 4, wherein the optical detector is a bar code reader and the indicia is a bar code.

7. The patient support apparatus of claim 6, wherein the indicia is at least two bar codes.

8. The patient support apparatus of claim 1, wherein the data is associated with a caregiver or a patient.

9. The patient support apparatus of claim 8, wherein the control system further includes a clock providing a date, the clock in communication with the processor and the set of instructions performed by the processor includes (iii) receiving the date from the clock and (iv) communicating the date to the network along with the linked data and unique identifier.

10. The patient support apparatus of claim 8, wherein the data is associated with a biologic sample.

11. The patient support apparatus of claim 1, wherein the network includes a hospital information system.

12. The patient support apparatus of claim 11, wherein the network further includes a nurse call system.

13. The patient support apparatus of claim 1, wherein the control system further includes a user interface in communication with the processor, the user interface having a display and at least one user input device, wherein the set of instructions performed by the processor further includes (iii) communicating a prompt to the display, (iv) receiving a response to the prompt from the user input device, and (v) communicating the response to the network along with the linked data and unique identifier.

14. The patient support apparatus of claim 1, wherein the control system further includes a receiver in communication with the network and the processor and a user interface in communication with the processor, the user interface having a display, wherein the set of instructions performed by the processor further includes (iii) receiving network information from the receiver and (iv) communicating the network information to the display of the user interface so that the display is reconfigured to show the network information.

15. The patient support apparatus of claim 14, wherein the network information is patient information.

16. A method of monitoring events at a patient support apparatus comprising the steps of
  detecting an indicia of a predetermined pattern with an optical detector, the indicia being spaced apart from the patient support apparatus, the optical detector communicating data that identifies a specific physical location of the patient support apparatus as determined from the indicia,
  linking the data communicated from the optical detector with a unique identifier for the patient support apparatus and a date,
  communicating the linked data, unique identifier, and date to a network.

17. The method of claim 16 further comprising the steps of displaying a prompt on a display and communicating a response to the prompt to the network along with the linked data, unique patient support identifier, and date.

18. The method of claim 16 wherein the response to the prompt is patient information.

19. The method of claim 16 further comprising the steps of receiving network information associated with the data from the network and displaying the network information on a display coupled to a patient support.

20. The method of claim 16 wherein the network information is patient information, caregiver information, technician information, or housekeeper information.

* * * * *